US012396679B2

(12) United States Patent
Metcalf et al.

(10) Patent No.: US 12,396,679 B2
(45) Date of Patent: Aug. 26, 2025

(54) SYSTEM AND METHOD FOR POST-OPERATIVE ASSESSMENT OF SPINAL MOTION AND IMPLANT-BASED STRAIN CORRELATION

(71) Applicant: Warsaw Orthopedic, Inc., Warsaw, IN (US)

(72) Inventors: Newton H. Metcalf, Memphis, TN (US); Nicholas Benson, Collierville, TN (US); Robert A. Fields, Memphis, TN (US); Arjun Siby-Kurian, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 815 days.

(21) Appl. No.: 17/666,782

(22) Filed: Feb. 8, 2022

(65) Prior Publication Data

US 2022/0160294 A1  May 26, 2022

Related U.S. Application Data

(63) Continuation of application No. 16/855,444, filed on Apr. 22, 2020, now abandoned, and a
(Continued)

(51) Int. Cl.
*A61B 5/00* (2006.01)
*A61B 5/01* (2006.01)
*A61B 5/11* (2006.01)

(52) U.S. Cl.
CPC .......... *A61B 5/4566* (2013.01); *A61B 5/0024* (2013.01); *A61B 5/01* (2013.01);
(Continued)

(58) Field of Classification Search
CPC ........................... A61B 5/0024; A61B 5/4566
See application file for complete search history.

(56) References Cited

U.S. PATENT DOCUMENTS

| 3,444,775 A | 5/1969 | Hills |
| 5,697,929 A | 12/1997 | Mellinger |
(Continued)

FOREIGN PATENT DOCUMENTS

| CN | 103140168 A | 6/2013 |
| CN | 110582229 A | 12/2019 |
(Continued)

OTHER PUBLICATIONS

European Search Report in U.S. Appl. No. 20/837,889 dated Apr. 25, 2023.
(Continued)

*Primary Examiner* — Daniel L Cerioni
(74) *Attorney, Agent, or Firm* — FOX ROTHSCHILD LLP (57) ABSTRACT

A system for assessing a status of a spinal implant includes a reader device, a wearable body sensor, and a spinal implant. The wearable body sensor includes a first short-range receiver, a first short-range transmitter, and an inertial measurement unit. The wearable body sensor is configured to be positioned over a portion of a spine of a wearer, and measure movement information corresponding to spinal motion of the wearer while the wearer performs one or more movements while wearing the wearable body sensor. The spinal implant includes one or more sensors configured to measure implant information comprising one or more characteristics of a fusion status of the spinal implant, a second short-range receiver, and a second short-range transmitter. The wearable body sensor is configured to communicate movement information to the reader device. The spinal
(Continued)

implant is configured to communicate implant information to the reader device via the second transmitter.

25 Claims, 5 Drawing Sheets

Related U.S. Application Data continuation-in-part of application No. 16/509,285, filed on Jul. 11, 2019, now abandoned, and a continuation-in-part of application No. 16/395,221, filed on Jul. 3, 2019, now Pat. No. 11,707,299, and a continuation-in-part of application No. 16/395,212, filed on Apr. 25, 2019, now Pat. No. 11,529,208, and a continuation-in-part of application No. 16/395,216, filed on Apr. 25, 2019, now Pat. No. 11,589,905, and a continuation-in-part of application No. 16/132,094, filed on Sep. 14, 2018, now Pat. No. 11,278,238, and a continuation-in-part of application No. 16/039,592, filed on Jul. 19, 2018, now Pat. No. 11,298,162.

(52) U.S. Cl.
CPC .......... *A61B 5/1126* (2013.01); *A61B 5/6833* (2013.01); *A61B 2560/0219* (2013.01); *A61B 2560/0468* (2013.01); *A61B 2562/0219* (2013.01); *A61B 2562/0247* (2013.01); *A61B 2562/0271* (2013.01)

(56) References Cited

U.S. PATENT DOCUMENTS

| | | |
|---|---|---|
| 6,004,349 A | 12/1999 | Jackson |
| 6,179,841 B1 | 1/2001 | Jackson |
| 6,280,445 B1 | 8/2001 | Morrison et al. |
| 6,485,491 B1 | 11/2002 | Farris et al. |
| 6,884,244 B1 | 4/2005 | Jackson |
| 7,357,037 B2 | 4/2008 | Hnat et al. |
| 7,993,269 B2 | 8/2011 | Donofrio et al. |
| 8,057,519 B2 | 11/2011 | Justis et al. |
| 8,372,147 B2 | 2/2013 | Roche |
| 8,868,200 B2 | 10/2014 | Abrahamson et al. |
| 9,241,738 B2 | 1/2016 | Quevedo et al. |
| 9,498,294 B2 | 11/2016 | Rigsby et al. |
| 9,585,602 B1 | 3/2017 | Navarro et al. |
| 9,711,840 B2 | 7/2017 | Lin |
| 10,219,699 B2 | 3/2019 | Wilder et al. |
| 2003/0073996 A1 | 4/2003 | Doubler et al. |
| 2005/0018749 A1 | 1/2005 | Sato et al. |
| 2005/0187549 A1 | 8/2005 | Jackson |
| 2005/0228326 A1 | 10/2005 | Kalfas et al. |
| 2005/0267477 A1 | 12/2005 | Jackson |
| 2006/0052782 A1 | 3/2006 | Morgan et al. |
| 2007/0017295 A1 | 1/2007 | Ohta et al. |
| 2007/0073300 A1 | 3/2007 | Attawia et al. |
| 2007/0100218 A1 | 5/2007 | Sweitzer et al. |
| 2008/0133009 A1 | 6/2008 | Caylor |
| 2008/0281212 A1 | 11/2008 | Nunez et al. |
| 2009/0198273 A1 | 8/2009 | Zhang et al. |
| 2009/0228074 A1 | 9/2009 | Edgell et al. |
| 2009/0234391 A1 | 9/2009 | Butler et al. |
| 2009/0298650 A1 | 12/2009 | Kutliroff |
| 2010/0152621 A1 | 6/2010 | Janna et al. |
| 2010/0201118 A1 | 8/2010 | Anton et al. |
| 2010/0217331 A1 | 8/2010 | Spagnoli et al. |
| 2010/0298886 A1 | 11/2010 | Kraus et al. |
| 2011/0106179 A1 | 5/2011 | Prevost et al. |
| 2011/0213221 A1 | 9/2011 | Roche |
| 2011/0319755 A1 | 12/2011 | Stein et al. |
| 2012/0059389 A1 | 3/2012 | Larson et al. |
| 2012/0143029 A1 | 6/2012 | Silverstein et al. |
| 2012/0221057 A1 | 8/2012 | Zhang et al. |
| 2013/0072982 A1 | 3/2013 | Simonson |
| 2013/0076157 A1 | 3/2013 | Stein |
| 2013/0079669 A1 | 3/2013 | Stein et al. |
| 2013/0079680 A1 | 3/2013 | Stein et al. |
| 2013/0096396 A1 | 4/2013 | Riedel |
| 2013/0253334 A1 | 9/2013 | Al-Ali et al. |
| 2014/0214097 A1 | 7/2014 | Jackson et al. |
| 2015/0080901 A1 | 3/2015 | Stein |
| 2015/0257687 A1 | 9/2015 | Pushpala et al. |
| 2016/0128573 A1 | 5/2016 | Wilder et al. |
| 2016/0235480 A1 | 8/2016 | Scholl et al. |
| 2016/0331415 A1 | 11/2016 | Serhan et al. |
| 2017/0007420 A1 | 1/2017 | Stevenson et al. |
| 2017/0079555 A1 | 3/2017 | Munro et al. |
| 2017/0138387 A1 | 5/2017 | Saigo et al. |
| 2017/0196499 A1 | 7/2017 | Hunter |
| 2017/0196508 A1 | 7/2017 | Hunter |
| 2017/0231559 A1 | 8/2017 | Cuevas et al. |
| 2018/0195547 A1 | 7/2018 | Demeocq |
| 2018/0310964 A1 | 11/2018 | Stevenson et al. |
| 2019/0038214 A1 | 2/2019 | Mikhail et al. |
| 2019/0344070 A1 | 11/2019 | Molnar et al. |
| 2019/0346313 A1 | 11/2019 | Cox |
| 2020/0022733 A1 | 1/2020 | Benson et al. |
| 2020/0022735 A1 | 1/2020 | Fields et al. |
| 2020/0022739 A1 | 1/2020 | Benson et al. |
| 2020/0022740 A1 | 1/2020 | Benson et al. |
| 2020/0022772 A1 | 1/2020 | Benson et al. |
| 2020/0069247 A1 | 3/2020 | Hunter |
| 2020/0085366 A1 | 3/2020 | Benson et al. |
| 2020/0297513 A1 | 9/2020 | Zellmer et al. |
| 2020/0330230 A1 | 10/2020 | Macewan et al. |
| 2020/0405239 A1 | 12/2020 | Trabish et al. |
| 2021/0153909 A1 | 5/2021 | Siby-Kurian et al. |
| 2021/0186567 A1 | 6/2021 | Bobbitt et al. |
| 2022/0378370 A1 | 12/2022 | Pasha |

FOREIGN PATENT DOCUMENTS

| | | |
|---|---|---|
| JP | 2015532841 A | 11/2015 |
| KR | 10-1851690 B1 | 4/2018 |
| WO | 2013109762 A1 | 7/2013 |
| WO | 15/200720 A2 | 12/2015 |
| WO | 2017006068 A1 | 1/2017 |
| WO | 2017007821 A1 | 1/2017 |
| WO | 2017165717 A1 | 9/2017 |
| WO | 2017180653 A1 | 10/2017 |
| WO | 2020018862 A1 | 1/2020 |

OTHER PUBLICATIONS

Karipott Salil Sidharthan et al: "An Embedded Wireless Temperature Sensor for Orthopedic Implants", IEEE Sensors Journal, IEEE, USA, vol. 18, No. 3, Feb. 1, 2018 (Feb. 1, 2018), pp. 1265-1272, XP011675608, ISSN: 1530-437X, DOI: 10.1109/JSEN.2017.2780226.
International Search Report and Written Opinion in Application No. PCT/IB2023/053705 dated Jul. 7, 2023.
International Search Report and Written Opinion in Application No. PCT/IB2023/053707 dated Jul. 24, 2023.
Chinese Office Action in Application No. 201980047442.2 dated Jun. 27, 2023.
International Search Report and Written Opinion in Application No. PCT/IB2023/053713 dated Jul. 28, 2023.
European Search Report in Application No. 19838911.6 dated Apr. 4, 2022.
European Search Report in Application No. 19838132.9 dated Apr. 4, 2022.
European Search Report in Application No. 19837036.3 dated Apr. 4, 2022.
European Search Report in Appln. No. 21168012.9 dated Sep. 20, 2021.
International Search Report for corresponding application No. PCT/US2019/050717 dated Sep. 12, 2019.
Rodriguez-Martin, et al. "A wearable inertial measurement unit for long-term monitoring in the dependency care area." Sensors 13.10 (2013): 14079-14104. (Year: 2016).

(56) References Cited

OTHER PUBLICATIONS

Conway, Justin, Christy C. Tomkins, and Andrew J. Haig. "Walking assessment in people with lumbar spinal stenosis: capacity, performance, and self-report measures." The Spine Journal 11.9 (2011): 816-823. (Year: 2011).
Trost, et al. "Conducting accelerometer-based activity assessments in field-based research." Medicine & Science in Sports & Exercise 37.11 (2005): S531-S543. (Year: 2005).
Liu, Ye, et al. "From action to activity: sensor-based activity recognition." Neurocomputing 181 (2016): 108-115. (Year: 2016).
Ahmadi, Amin, et al. "Automatic activity classification and movement assessment during a sports training session using wearable inertial sensors." 2014 11th International Conference on Wearable and Implantable Body Sensor Networks. IEEE, 2014. (Year: 2014).
International Search Report, PCT/US2019/042511, Oct. 31, 2019.
International Search Report, PCT/US2019/042516, Oct. 31, 2019.
International Search Report and Written Opinion, PCT/US2020/041487 mailed Nov. 2, 2020.
Chinese Office Action in Application No. 202110429353.3 dated Feb. 17, 2025.

SYSTEM AND METHOD FOR POST-OPERATIVE ASSESSMENT OF SPINAL MOTION AND IMPLANT-BASED STRAIN CORRELATION

CROSS-REFERENCE TO RELATED U.S. PATENT APPLICATIONS

This application is a continuation of U.S. application Ser. No. 16/855,444, filed Apr. 22, 2020, entitled "SYSTEM AND METHOD FOR POST-OPERATIVE ASSESSMENT OF SPINAL MOTION AND IMPLANT BASED STRAIN CORRELATION," and a continuation in-part of U.S. application Ser. No. 16/509,285, filed Jul. 11, 2019, entitled "TEMPERATURE SENSING ARRAY FOR SET SCREW INFECTION," and a continuation in-part of U.S. application Ser. No. 16/395,221, filed Jul. 3, 2019, entitled "ANTENNA PLACEMENT FOR A DIGITAL SET SCREW," and a continuation in-part of U.S. application Ser. No. 16/395,212, filed Apr. 25, 2019, entitled "BREAK-OFF SET SCREW," and a continuation in-part of U.S. application Ser. No. 16/395,216, filed Apr. 25, 2019, entitled "SET SCREW SENSOR PLACEMENT," and a continuation in-part of U.S. application Ser. No. 16/039,592, filed Jul. 19, 2018, entitled "LOAD SENSING ASSEMBLY FOR A SPINAL IMPLANT," and a continuation in-part of U.S. application Ser. No. 16/132,094, filed Sep. 14, 2018, entitled "WEARABLE SENSOR DEVICE AND ANALYSIS PLATFORM FOR OBJECTIVE OUTCOME ASSESSMENT IN SPINAL DISEASES," all of which are incorporated herein by reference in their entirety.

TECHNICAL FIELD

The present disclosure generally relates to a wearable body sensor that is used in connection with one or more spinal implant-based sensors to assess strain data pertaining to spinal implants.

BACKGROUND

Treatment of spinal disorders, such as degenerative disc disease, disc herniations, scoliosis or other curvature abnormalities, and fractures, often requires surgical treatments. For example, spinal fusion may be used to limit motion between vertebral members. As another example, implants may be used to preserve motion between vertebral members.

A patient's spinal condition is generally evaluated using a combination of patient feedback, imaging technologies and clinician evaluations. Since data pertaining to a patient's movement can contain valuable information about the health of the patient's neurological function and musculoskeletal health, it is desirable to obtain this information in an objective rather than subjective manner.

SUMMARY

In an embodiment, a system for assessing a status of a spinal implant includes a reader device, a wearable body sensor, and a spinal implant. The wearable body sensor includes a first short-range receiver, a first short-range transmitter, and an inertial measurement unit. The wearable body sensor is configured to be positioned over at least a portion of a spine of a wearer, and measure movement information corresponding to spinal motion of the wearer while the wearer performs one or more movements while wearing the wearable body sensor. The spinal implant includes one or more sensors configured to measure implant information comprising one or more characteristics of a fusion status of the spinal implant, a second short-range receiver, and a second short-range transmitter. The wearable body sensor is configured to communicate at least a portion of the movement information to the reader device. The spinal implant is configured to communicate at least a portion of the implant information to the reader device via the second transmitter.

The wearable body sensor may be affixed to the wearer via an adhesive. The wearable body sensor may include a mobile electronic device.

The one or more movements may be part of a protocol.

The one or more sensors may include a load sensing assembly configured to detect a strain experienced by the spinal implant. The one or more sensors may include a pressure sensor. The one or more sensors may include a second inertial measurement unit. The one or more sensors may include a temperature sensor.

The reader device may be configured to transmit at least a portion of the movement information and/or the implant information to one or more electronic devices.

The wearable body sensor may be configured to communicate at least a portion of the movement information to the reader device when the reader device is located within a short-range communication distance from the wearable body sensor. The spinal implant may be configured to communicate at least a portion of the implant information to the reader device when the reader device is located within a short-range communication distance from the spinal implant. The reader device may be further configured to transmit power to the spinal implant.

In an embodiment, a system for assessing a status of a spinal implant includes a reader device, a wearable body sensor in communication with the reader device, and one or more spinal implants. The wearable body sensor includes a first short-range receiver, a first short-range transmitter, and an inertial measurement unit. Each of the one or more spinal implants includes one or more sensors configured to measure implant information comprising one or more characteristics of a fusion status of the spinal implant, a second short-range receiver, and a second short-range transmitter. Each spinal implant is in communication with the reader device.

The wearable body sensor may be configured to be positioned over at least a portion of a spine of a wearer and measure movement information corresponding to spinal motion of the wearer while the wearer performs one or more movements while wearing the wearable body sensor.

The wearable body sensor may be configured to communicate at least a portion of the movement information to the reader device.

Each spinal implant may be configured to communicate at least a portion of the implant information to the reader device via the second transmitter. The wearable body sensor may be affixed to a wearer via an adhesive. The wearable body sensor may be a mobile electronic device.

The one or more movements may be part of a protocol.

The one or more sensors may include a load sensing assembly configured to detect a strain experienced by the spinal implant. The one or more sensors may include a pressure sensor. The one or more sensors may include a second inertial measurement unit. The one or more sensors may include a temperature sensor.

The reader device may be configured to transmit at least a portion of the movement information and/or the implant information to one or more electronic devices. The wearable body sensor may be configured to communicate at least a portion of the movement information to the reader device when the reader device is located within a short-range communication distance from the wearable body sensor.

The spinal implant may be configured to communicate at least a portion of the implant information to the reader device when the reader device is located within a short-range communication distance from the spinal implant.

The reader device may be configured to transmit power to the spinal implant.

DETAILED DESCRIPTION

In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Generally, similar spatial references of different aspects or components indicate similar spatial orientation and/or positioning, i.e., that each "first end" is situated on or directed towards the same end of the device. Further, the use of various spatial terminology herein should not be interpreted to limit the various insertion techniques or orientations of the implant relative to the positions in the spine.

The following terms shall have, for purposes of this application, the respective meanings set forth below:

A "computing device", "electronic device", or "computer" refers to a device or system that includes a processor and memory. Each device may have its own processor and/or memory, or the processor and/or memory may be shared with other devices as in a virtual machine or container arrangement. The memory will contain or receive programming instructions that, when executed by the processor, cause the electronic device to perform one or more operations according to the programming instructions. Examples of electronic devices include personal computers, servers, mainframes, virtual machines, containers, mobile electronic devices such as smartphones, Internet-connected wearables, tablet computers, laptop computers, and appliances and other devices that can communicate in an Internet-of-things arrangement. In a client-server arrangement, the client device and the server are electronic devices, in which the server contains instructions and/or data that the client device accesses via one or more communications links in one or more communications networks. In a virtual machine arrangement, a server may be an electronic device, and each virtual machine or container also may be considered an electronic device. In the discussion below, a client device, server device, virtual machine or container may be referred to simply as a "device" for brevity. Additional elements that may be included in electronic devices will be discussed below in the context of FIG. 6.

The terms "memory," "computer-readable medium" and "data store" each refer to a non-transitory device on which computer-readable data, programming instructions or both are stored. Unless the context specifically states that a single device is required or that multiple devices are required, the terms "memory," "computer-readable medium" and "data store" include both the singular and plural embodiments, as well as portions of such devices such as memory sectors.

Figure 1:
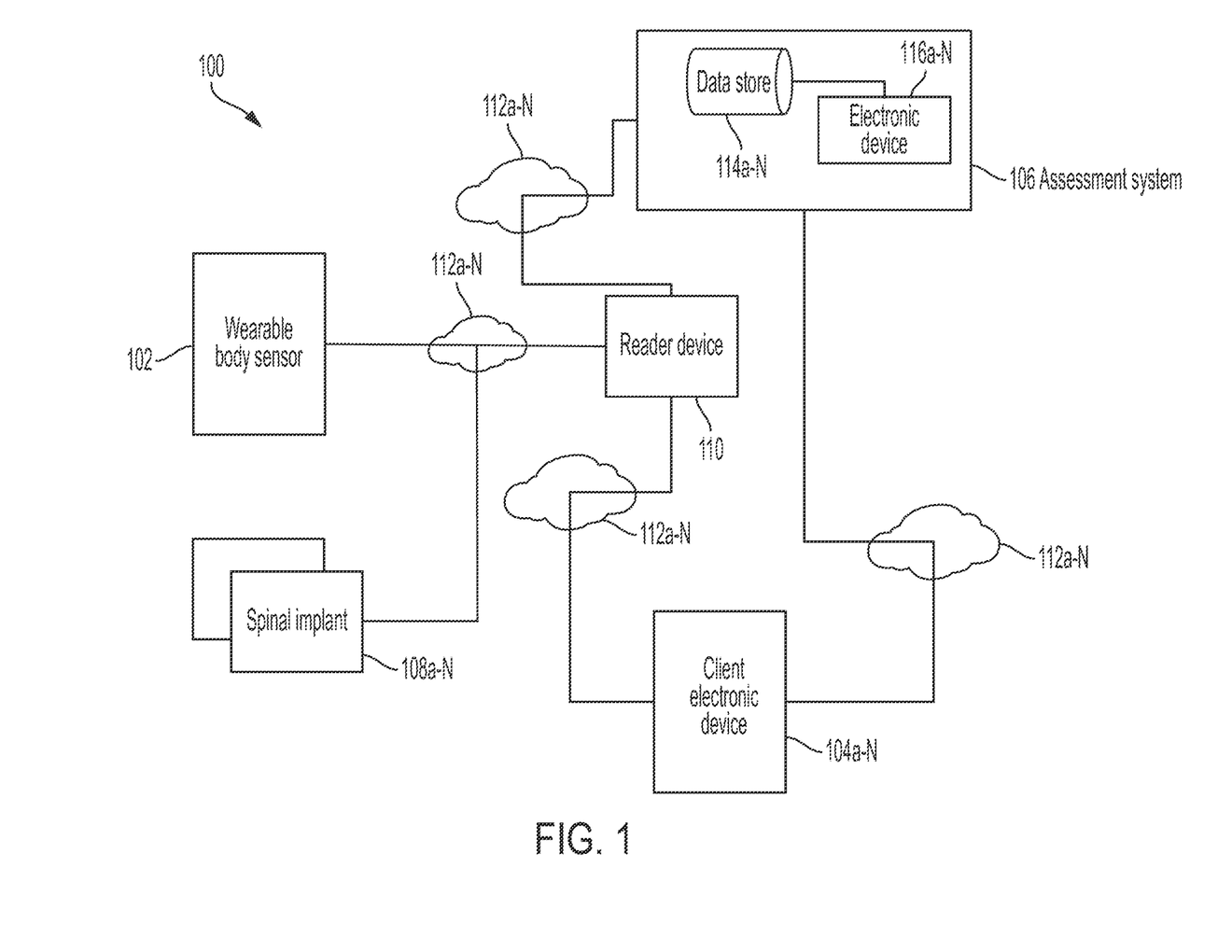
FIG. 1 illustrates an example spinal evaluation system.

FIG. 1 illustrates an example spinal evaluation system according to an embodiment. As illustrated by FIG. 1, the system 100 includes a wearable body sensor 102, one or more client electronic devices 104a-N, an assessment system 106, one or more spinal implants 108a-N, and a reader device 110.

The reader device 110 may be in communication with the wearable body sensor 102 and/or one or more spinal implants 108a-N via one or more communication networks 112a-N. The reader device may be in communication with one or more client electronic devices 104a-N and/or the assessment system 106 via one or more communication networks 112a-N. In various embodiments, one or more of the client electronic devices 104a-N may be in communication with the assessment system 106 via one or more communication networks 112a-N. A communication network 112a-N may be a local area network (LAN), a wide area network (WAN), a mobile or cellular communication network, an extranet, an intranet, the Internet, a short range communication network and/or the like. Although FIG. 1 shows separate communication networks 112a-N it is to be understood that these networks, or some combination of these networks, may be implemented as a single communication network.

In various embodiments, the reader device 110 may include a power source, a processing device, and/or one or more communication devices. The power source of the reader device 110 may be a battery. The processing device may be a processor, a microprocessor, and/or the like. The communication devices may include a short-range transmitter, receiver, and/or transceiver. As will be explained in more detail below, a reader device 110 may communicate with the wearable body sensor 102 and/or one or more spinal implants 108a-N via one or more short range communication protocols. In various embodiments, examples of reader devices 110 may include, without limitation, RFID reader devices, NFC reader devices, and/or the like.

The communication devices may include a transmitter, a receiver, and/or a transceiver that may be used to facilitate wireless communication between the reader device 110 and one or more electronic devices over a wireless network such as, for example, the Internet or an intranet. For example, a reader device may communicate with one or more client electronic devices 104a-N and/or the assessment system 106.

Figure 2A:
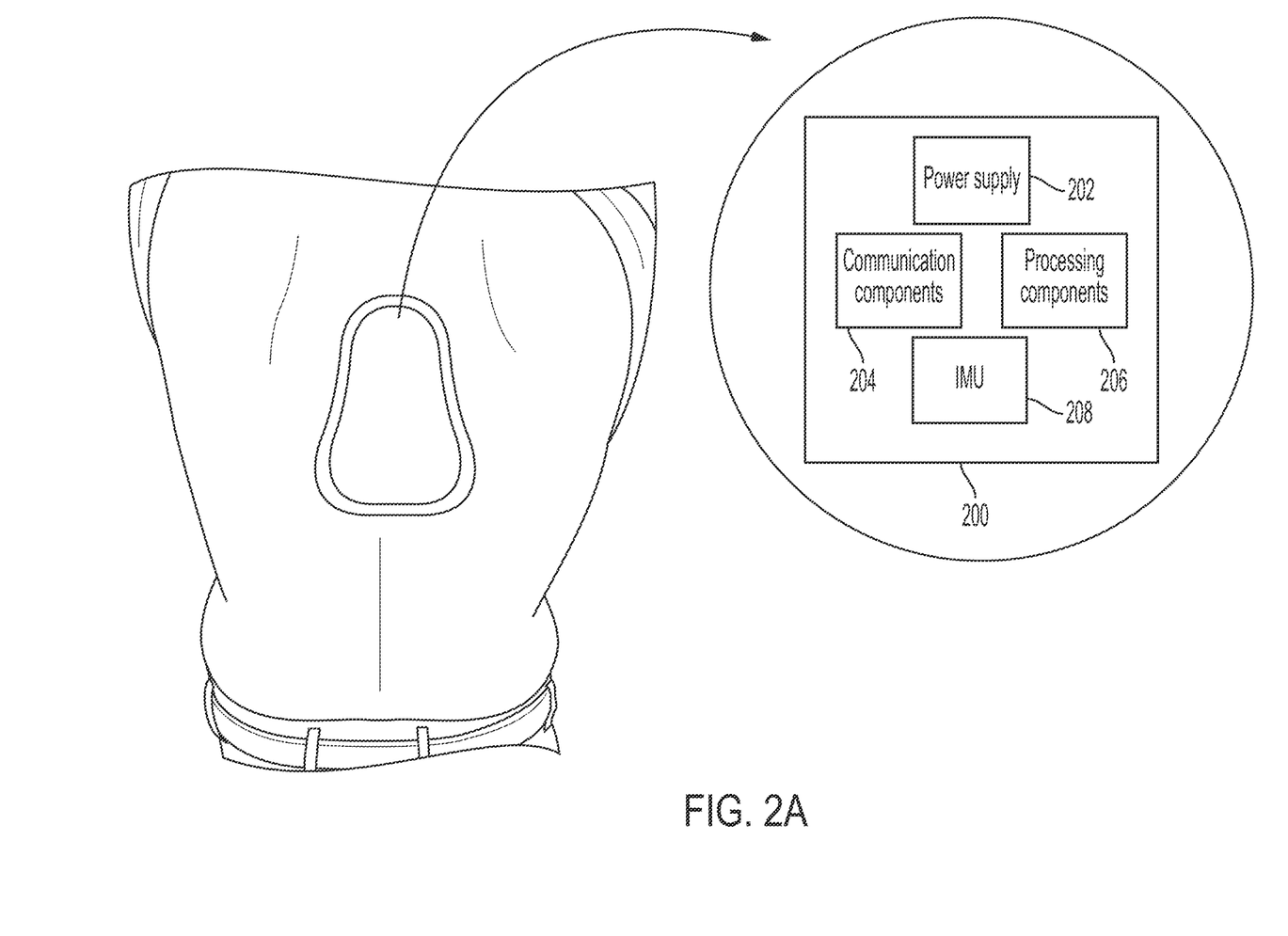
FIGS. 2A and 2B each illustrates an example of a wearable body sensor.

FIG. 2A illustrates an example of a wearable body sensor 102 according to an embodiment. A wearable body sensor 102 may be an electronic device configured to be worn by an individual. For example, as illustrated in FIG. 2A, a wearable body sensor 102 may be a patch. A wearable body sensor 102 may be configured to be worn by an individual across at least a portion of the individual's spine, such as a portion of an individual's lower back, a portion of an individual's middle back, a portion of an individual's upper back, and/or the like. A wearable body sensor 102 may be secured to an individual using an adhesive as illustrated in FIG. 2A. However, it is understood that other ways of securing or affixing a wearable body sensor 102 to an individual may be used within the scope of this disclosure.

For instance, a wearable body sensor 102 may be secured to an individual via one or more straps, braces, and/or the like. For example, a mobile electronic device, such as a mobile phone, may be a wearable body sensor and may be secured to an individual such that the mobile electronic device is positioned over at least a portion of the individual's spine with one or more straps or belts, as illustrated for example in FIG. 2B. In some embodiments, a wearable body sensor 102 may be part of a wearable garment such as, for example, a harness, a belt, a vest, a shirt, and/or the like. U.S. patent application Ser. No. 16/132,094, which is incorporated herein by reference in its entirety, describes example wearable electronic devices and systems which may be used within the scope of this disclosure.

Figure 2B:
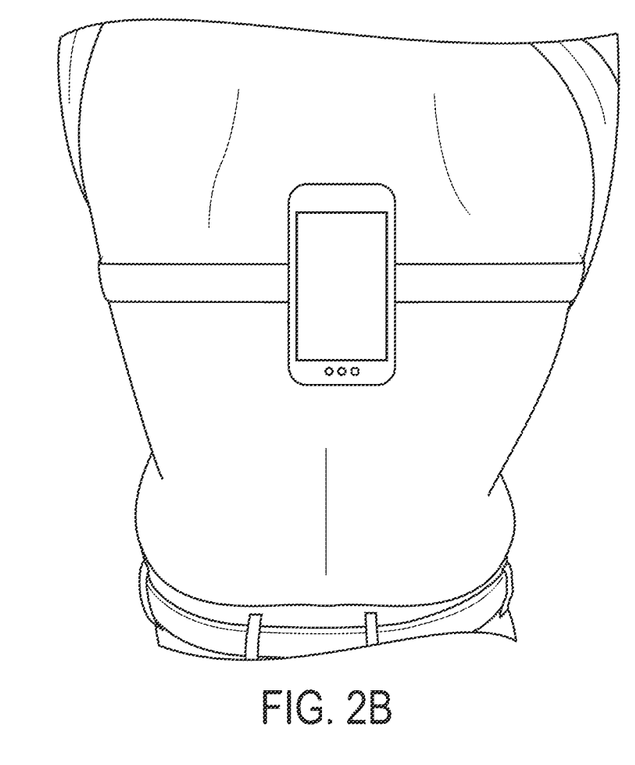

In various embodiments, a wearable body sensor 102 may include an electronics system. As illustrated in FIG. 2, an electronics system 200 may be embedded into at least a portion of the wearable body sensor 102. The electronics system 200 may include a power supply 202, one or more communication components 204, one or more processing components 206, one or more inertial measurement units (IMU) 208 and/or the like.

The power supply 202 may include a battery. The communication components 204 may include one or more short-range communication components such as, for example, a short-range transmitter, receiver and/or transceiver. The communication components 204 may include one or more other communication components such as, for example, a receiver, a transmitter, and/or a transceiver that may be used to facilitate wireless communication between the electronics system 200 and one or more electronic devices over a wireless network such as, for example, the Internet or an intranet.

The processing components 206 may include one or more processing devices such as, for example, a processor, a microprocessor, and/or the like. The IMUs 208 may include one or more accelerometers, gyroscopes, magnetometers, and/or the like.

The electronics system 200 of a wearable body sensor 102 may be positioned on a portion of the wearable apparatus that overlaps at least a portion of a wearer's spine, or is near to or in proximity to a wearer's spine, when worn. For example, FIG. 2 illustrates an example placement of an electronics system 200 according to an embodiment. However, it is understood that an electronics system, or a portion of an electronics system, may be located elsewhere on the wearable apparatus.

In various embodiments, a wearable body sensor 102 may include one or more integrated circuits, microchips or other memory devices. For instance, a wearable body sensor 102 may include a memory chip that may be removed from the wearable apparatus and inserted into another electronic device in order to transfer data stored on the memory chip. A wearable body sensor 102 may also include firmware and/or a battery, including for example a thin film battery that may be encapsulated or may include a piezo-electronic powering. In various embodiments, a wearable body sensor 102 may include an NFC chip, and RFID chip, and/or the like.

Referring back to FIG. 1, in various embodiments, the wearable body sensor 102 may be in communication with one or more spinal implants 108a-N. A spinal implant may be a medical device used for the treatment of one or more musculoskeletal disorders. Examples of spinal implants 108a-N may include, without limitation, vertebral fixation screws, pedicle screws, hooks, cross connectors, offset connectors and related systems for use during various spinal procedures or other orthopedic procedures and that may be used in conjunction with other devices and instruments related to spinal treatment, such as rods, wires, plates, intervertebral implants, and other spinal or orthopedic implants, insertion instruments, specialized instruments such as, for example, delivery devices (including various types of cannula) for the delivery of these various spinal or other implants to the vertebra or other areas within a patient in various directions, and/or a method or methods for treating a spine, such as open procedures, mini-open procedures, or minimally invasive procedures. A spinal implant 108a-N may include one or more sensors. A sensor may be configured to detect and/or measure one or more characteristics associated with the spinal implant 108a-N. Example sensors include, without limitation, a load sensing assembly for detecting the strain experienced by an spinal implant. U.S. patent application Ser. Nos. 16/039,592, 16/395,212, 16/395,216, 16/395,221, and 16/509,285, each of which is incorporated herein by reference in its entirety, describe example load sensing assemblies which may be used within the scope of this disclosure. Other examples of sensors may include, without limitation, a pressure sensor, a temperature sensor, an IMU, a gyroscope, and/or the like.

U.S. Pat. Nos. 6,485,491 and 8,057,519, as well as U.S. patent application Ser. Nos. 16/039,592, 16/395,212, 16/395,216, 16/395,221, and 16/509,285, each incorporated herein by reference in its entirety, describe example spinal implants that may be used within the scope of this disclosure. Other example spinal implants may include, without limitation, interbody fusion devices such as, for example, fusion cages.

A spinal implant 108a-N may include a receiver, a transmitter, and/or a transceiver. A receiver, a transmitter, and/or a transceiver may be a near-field communication (NFC) or other short-range communication receiver, transmitter, and/or transceiver such as, for example, a radio frequency identification (RFID) coil, an NFC antenna, and/or the like. In various embodiments, a receiver, transmitter, and/or transceiver may be part of an integrated circuit such as, for example, an RFID chip, and NFC chip, and/or the like.

An assessment system 106 may include one or more electronic devices such as, for example, servers and/or one or more data stores. For instance, as shown in FIG. 1, an assessment system 106 may include one or more electronic devices 116a-N and one or more data stores 114a-N. A data store 114a-N may store measured data that is received from one or more sensors such as, for example, movement data, spinal implant performance information, and/or the like. A data store 114a-N may store movement information that it receives from a wearable apparatus 102. A data store 114a-N may store data so that it is correlated to a particular subject.

In various embodiments, one or more sensors of a spinal implant 108a-N may measure one or more effects of a subject's movement on the spinal implant. This movement or motion may be of a wearer's spinal axis, lower limbs, rotations, bending and/or the like.

A client electronic device 104a-N may be a smartphone, a tablet, a laptop, a computing device or other electronic device. For instance, a client electronic device 104a-N may be a smartphone or tablet associated with a subject. As another example, a client electronic device 104a-N may be a smartphone or tablet associated with a clinician, healthcare provider, healthcare entity and/or the like.

Figure 3:
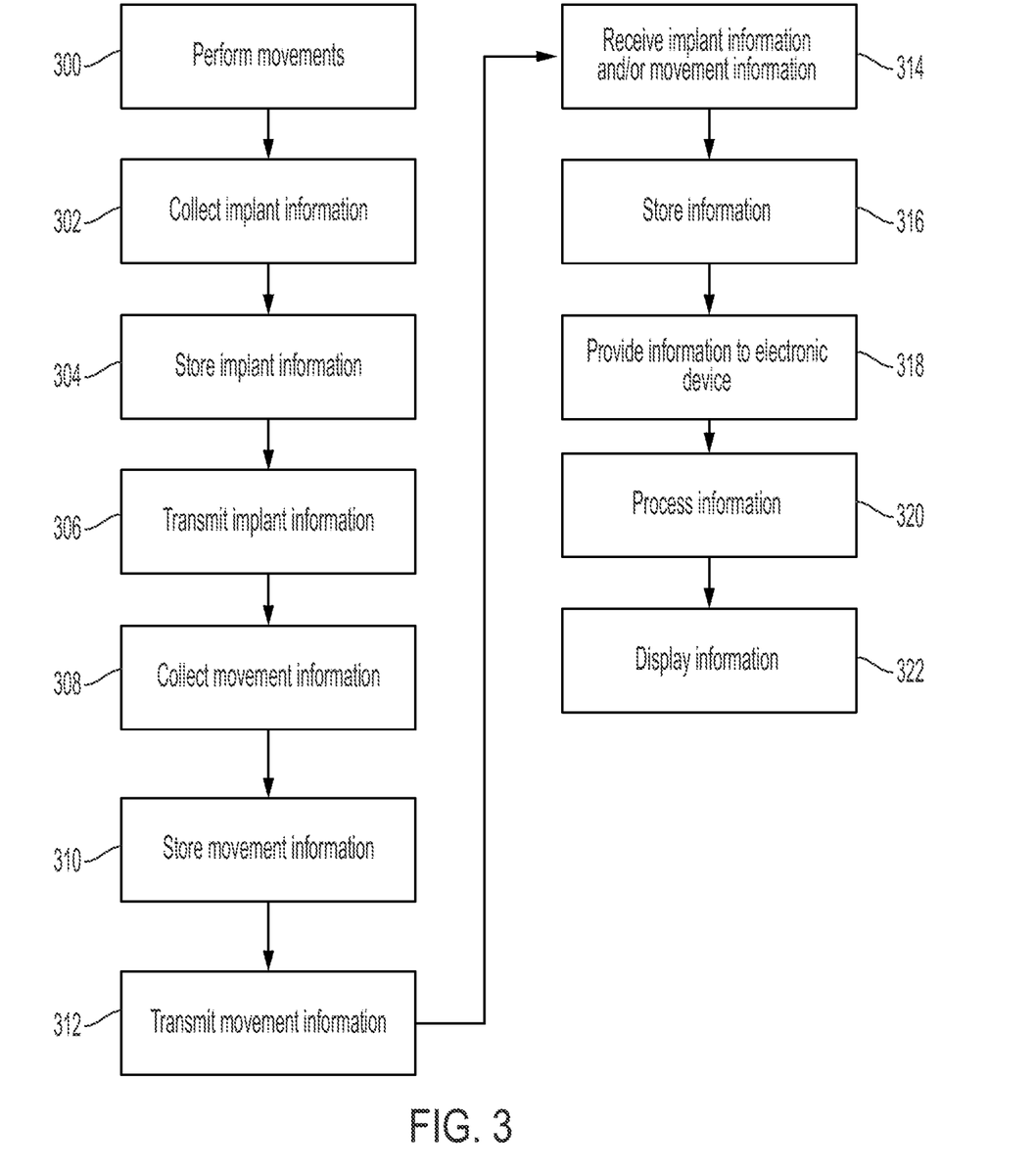
FIG. 3 illustrates a flow chart of an example method of obtaining subject information.

FIG. 3 illustrates a flow chart of an example method of obtaining subject information according to an embodiment. A subject may apply a wearable body sensor. The subject may then perform 300 one or more movements or types of movements while wearing the wearable body sensor.

A subject may wear a wearable body sensor for a limited period of time, such as, for example, in a clinical setting, during an evaluation with a clinician, and/or the like. In this situation, a subject may be asked to perform one or more movements, activities or protocols to gather information about the subject's movement. For instance, a clinician may ask a subject to sit, stand, walk, bend over, rotate, turn, lay down or perform other activities while wearing a wearable body sensor.

While the subject is performing one or more movements, one or more sensors of one or more spinal implants implanted within the subject may measure or collect 302 implant information pertaining to one or more characteristics of the associated spinal implant during such movements. For example, a spinal implant may include one or more strain gauges or strain sensors. These sensors may measure strain or one or more strain patterns experienced by the implant during one or more movements or across a range of movements. As another example, a spinal implant may include an IMU which may measure movement information during one or more movements or across a range of movements. In another example, a spinal implant may include a gyroscope which may measure an orientation of a wearer's back or trunk. In another example, a spinal implant may include a pressure sensor that may measure pressure variations on or within the spinal implant. For instance, a set screw of a spinal implant may include a pressure sensor which may measure pressure and/or pressure variations in the chamber of the implant. In another embodiments, a spinal implant may include a temperature sensor which may measure the temperature or temperature variations of the spinal implant or of the area around the spinal implant. Additional and/or alternate sensors and/or measurements may be used and/or made within the scope of this disclosure.

One or more of the spinal implants of the subject may store 304 such implant information. One or more of the spinal implants may transmit 306 at least a portion of such implant information to the reader device when the reader device is within short-range communication distance from the spinal implants. A spinal implant may transmit 306 implant information to a reader device via a short-range transmitter or transceiver.

While the subject is performing one or more movements, the wearable body sensor may measure or collect 308 information pertaining to the subject's spinal movement during such movements. Movement information may include one or more characteristics associated with a subject's movement. For example, an IMU may provide information pertaining to the motion of the person wearing the wearable apparatus given the IMU and its placement. The raw x/y/z measurements may, for example, provide only information about the movement of the sensor itself, which may be different from the movement of a wearer. For example, known approaches utilize motion sensors that are integrated into devices such as phones and watches, which move considerably different ways and ways that are independent of their wearers or carriers.

One or more data points of data may have one or more associated parameters such as an associated timestamp, an associated velocity value, an associated barometric pressure value, and associated acceleration value, a rotation value, an orientation value and/or the like.

The wearable body sensor may store 310 such movement information. It may transmit 312 at least a portion of the movement information to the reader device when the reader device is within a short-range communication distance from the body sensor. The body sensor may transmit 312 movement information to a reader device via a short-range transmitter or transceiver.

The reader device may receive 314 implant information from one or more spinal implants and/or movement information from the body sensor. For example, a reader device may receive 314 implant information and/or movement information via a short-range receiver or transceiver. In various embodiments, a reader device may store 316 at least a portion of implant information and/or movement information received from one or more spinal implants and/or the wearable body sensor. A reader device may store 316 at least a portion of received implant information in one or more data stores.

In various embodiments, the wearable body sensor and/or one or more of the spinal implants may send information to the reader device when the reader device is placed within a certain distance from the wearable body sensor and/or one or more of the spinal implants. For example, the wearable body sensor may send information to the reader device when the reader device is located with 3-6 inches from the wearable body sensor. As another example, a spinal implant may send information to the reader device when the reader device is with 3-5 inches from the spinal implant. Other distances and/or distance ranges may be used within the scope of this disclosure. In various embodiments, a wearable body sensor and/or a spinal implant may communicate with a reader device or other electronic device without being interrogated.

The reader device may serve as a remote power source for one or more spinal implants. An electromagnetic field may be generated by the reader device (e.g., a transmitting coil) to transmit power across the skin of a subject to one or more spinal implants. A spinal implant may use the received energy to power or charge the implant.

The reader device may provide 318 at least a portion of the movement information and/or the implant information to an electronic device. For example, a reader device may provide 318 at least a portion of the movement information and/or the implant information to one or more client electronic devices and/or one or more electronic devices associated with an assessment system. In an embodiment, movement information and/or implant information may be provided 318 to an electronic device by removing a memory chip or other data store from a reader device, and connecting it to an electronic device. Alternatively, a reader device may transmit at least a portion of collected implant information and/or movement information to an electronic device via one or more communication networks. In some embodiments, a reader device may transmit information to an electronic device at certain times or intervals. In other embodiments, a reader device may transmit information to an electronic device in response to receiving a request from the electronic device.

One or more electronic devices, such as ones associated with an assessment system, may process 320 at least a portion of the implant information and/or the movement information. In various embodiments, an electronic device may process 320 information to assess one or more characteristics or a status of a spinal implant. Characteristics may be indicative of one or more anomalies or potential issues with one or more spinal implants. For instance, information may be used to determine whether an implant is experiencing unusual or anomalous strain during certain movements. The information may be used to detect a fusion status of a subject's spine, whether a spinal implant has failed or malfunctioned, and/or the like. This information may provide valuable insight into the construct and fusion status of an implant.

For example, as a successful spinal implant fusion matures, there is less strain on the hardware of the implant because the bone takes on the load from the implant. If the spinal implant is still experiencing a certain strain level or strain pattern after a certain period of time, it may be a sign of an issue with the fusion status of the implant.

As another example, if a spinal implant is experiencing pressure that exceeds a certain threshold value or is outside of a range of expected values, this may be an indication that there is swelling around the implant. Similarly, if a temperature sensor of a spinal implant measures a temperature that exceeds a certain threshold value or is outside of a range of values, this may be an indication of an infection in an area around the spinal implant.

In various embodiments, an assessment system may cause information pertaining to one or more characteristics or status of a spinal implant to be displayed 322 on one or more electronic devices. For instance, an assessment system may cause an indication of a spinal implant that is experiencing atypical characteristics to be displayed on a tablet associated with the subject's clinician. The displayed information may include one or more measurements from one or more of the spinal implant sensors such as, for example, strain measurements, pressure measurements, temperature measurements, and/or the like. A clinician may use the information to determine whether any changes to any spinal implant need to be made, or to make other treatment recommendations for the wearer.

Figure 4:
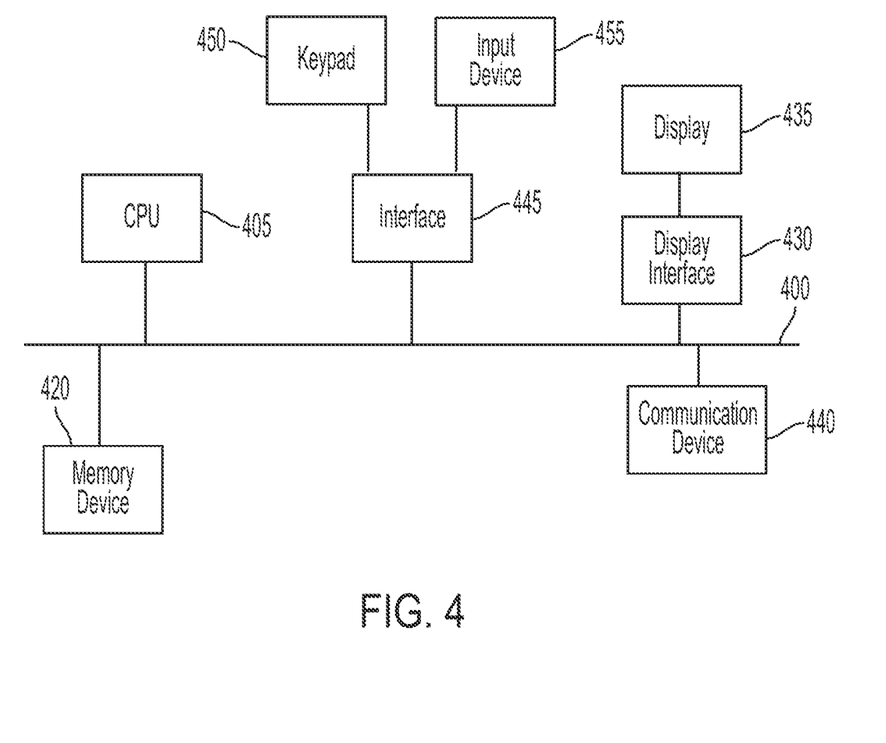
FIG. 4 depicts a block diagram of an example of internal hardware that may be used to contain or implement program instructions according to an embodiment.

FIG. 4 illustrates example hardware that may be used to contain or implement program instructions. A bus 400 serves as the main information highway interconnecting the other illustrated components of the hardware. CPU 405 is the central processing unit of the system, performing calculations and logic operations required to execute a program. CPU 405, alone or in conjunction with one or more of the other elements disclosed in FIG. 4, is an example of a processor as such term is used within this disclosure. Read only memory (ROM) and random access memory (RAM) constitute examples of non-transitory computer-readable storage media 420, memory devices or data stores as such terms are used within this disclosure.

Program instructions, software or interactive modules for providing the interface and performing any querying or analysis associated with one or more data sets may be stored in the memory device 420. Optionally, the program instructions may be stored on a tangible, non-transitory computer-readable medium such as a compact disk, a digital disk, flash memory, a memory card, a USB drive, an optical disc storage medium and/or other recording medium.

An optional display interface 430 may permit information from the bus 400 to be displayed on the display 435 in audio, visual, graphic or alphanumeric format. Communication with external devices may occur using various communication ports 440. A communication port 440 may be attached to a communications network, such as the Internet or an intranet.

The hardware may also include an interface 445 which allows for receipt of data from input devices such as a keypad 450 or other input device 455 such as a touch screen, a remote control, a pointing device, a video input device and/or an audio input device.

It will be appreciated that the various above-disclosed and other features and functions, or alternatives thereof, may be desirably combined into many other different systems or applications or combinations of systems and applications. Also that various presently unforeseen or unanticipated alternatives, modifications, variations or improvements therein may be subsequently made by those skilled in the art which are also intended to be encompassed by the following claims.

What is claimed is:

1. A system for assessing a status of a spinal implant, the system comprising:
    a reader device;
    a wearable body sensor comprising:
        a first short-range receiver,
        a first short-range transmitter, and
        an inertial measurement unit,
    wherein the wearable body sensor is configured to:
        be positioned over at least a portion of a spine of a wearer,
        measure movement information corresponding to spinal motion of the wearer while the wearer performs one or more movements while wearing the wearable body sensor, and
    a spinal implant comprising:
        one or more sensors configured to measure implant information comprising one or more characteristics of a fusion status of the spinal implant,
        a second short-range receiver, and
        a second short-range transmitter,
    wherein the wearable body sensor is configured to communicate at least a portion of the movement information to the reader device,
    wherein the spinal implant is configured to communicate at least a portion of the implant information to the reader device via the second short-range transmitter.

2. The system of claim 1, wherein the wearable body sensor is affixed to the wearer via an adhesive.

3. The system of claim 1, wherein the wearable body sensor comprises a mobile electronic device.

4. The system of claim 1, wherein the one or more movements are part of a protocol.

5. The system of claim 1, wherein the one or more sensors comprise a load sensing assembly configured to detect a strain experienced by the spinal implant.

6. The system of claim 1, wherein the one or more sensors comprises a temperature sensor.

7. The system of claim 1, wherein the reader device is further configured to transmit at least a portion of the movement information and/or the implant information to one or more electronic devices.

8. The system of claim 1, wherein the wearable body sensor is configured to communicate at least a portion of the movement information to the reader device when the reader device is located within a short-range communication distance from the wearable body sensor.

9. The system of claim 1, wherein the spinal implant is configured to communicate at least a portion of the implant information to the reader device when the reader device is located within a short-range communication distance from the spinal implant.

10. The system of claim 1, wherein the reader device is further configured to transmit power to the spinal implant.

11. A system for assessing a status of a spinal implant, the system comprising:
a reader device;
a wearable body sensor in communication with the reader device, wherein the wearable body sensor comprises:
a first short-range receiver,
a first short-range transmitter,
an inertial measurement unit, and
one or more spinal implants, each comprising:
one or more sensors configured to measure implant information comprising one or more characteristics of a fusion status of the spinal implant,
a second short-range receiver, and
a second short-range transmitter,
wherein each spinal implant is in communication with the reader device.

12. The system of claim 11, wherein:
the wearable body sensor is configured to be positioned over at least a portion of a spine of a wearer and measure movement information corresponding to spinal motion of the wearer while the wearer performs one or more movements while wearing the wearable body sensor.

13. The system of claim 12, wherein the wearable body sensor is configured to communicate at least a portion of the movement information to the reader device.

14. The system of claim 11, wherein each spinal implant is configured to communicate at least a portion of the implant information to the reader device via the second short-range transmitter.

15. The system of claim 11, wherein the wearable body sensor is affixed to a wearer via an adhesive.

16. The system of claim 11, wherein the wearable body sensor comprises a mobile electronic device.

17. The system of claim 12, wherein the one or more movements are part of a protocol.

18. The system of claim 11, wherein the one or more sensors comprise a load sensing assembly configured to detect a strain experienced by the spinal implant.

19. The system of claim 11, wherein the one or more sensors comprises a temperature sensor.

20. The system of claim 12, wherein the reader device is further configured to transmit at least a portion of the movement information and/or the implant information to one or more electronic devices.

21. The system of claim 12, wherein the wearable body sensor is configured to communicate at least a portion of the movement information to the reader device when the reader device is located within a short-range communication distance from the wearable body sensor.

22. The system of claim 11, wherein the spinal implant is configured to communicate at least a portion of the implant information to the reader device when the reader device is located within a short-range communication distance from the spinal implant.

23. The system of claim 11, wherein the reader device is further configured to transmit power to the spinal implant.

24. The system of claim 1, wherein the reader device is configured to:
receive the movement information from the wearable body sensor;
receive the implant information from the spinal implant; and
process the implant information and the movement information to determine strain experienced by the spinal implant during the one or more movements.

25. The system of claim 24, wherein the reader device is further configured to assess fusion status by determining if the spinal implant is experiencing anomalous strain during certain movements.

* * * * *